US009880108B2

(12) United States Patent
Gladnick

(10) Patent No.: US 9,880,108 B2
(45) Date of Patent: Jan. 30, 2018

(54) BORE IMAGING SYSTEM

(71) Applicant: Mitutoyo Corporation, Kanagawa-ken (JP)

(72) Inventor: Paul Gerard Gladnick, Seattle, WA (US)

(73) Assignee: Mitutoyo Corporation, Kanagawa-ken (JP)

( * ) Notice: Subject to any disclaimer, the term of this patent is extended or adjusted under 35 U.S.C. 154(b) by 510 days.

(21) Appl. No.: 14/581,847

(22) Filed: Dec. 23, 2014

(65) Prior Publication Data

US 2016/0178533 A1   Jun. 23, 2016

(51) Int. Cl.
*G01V 3/00* (2006.01)
*G01N 21/954* (2006.01)
*G02B 23/26* (2006.01)

(52) U.S. Cl.
CPC ........... *G01N 21/954* (2013.01); *G02B 23/26* (2013.01); *G01N 2021/9546* (2013.01)

(58) Field of Classification Search
USPC ........................................................ 324/318
See application file for complete search history.

(56) References Cited

U.S. PATENT DOCUMENTS

| | | | | |
|---|---|---|---|---|
| 4,674,834 A | * | 6/1987 | Margolin | G02B 6/06 250/227.2 |
| 4,760,421 A | * | 7/1988 | Margolin | G02B 6/06 250/227.2 |
| 4,762,391 A | * | 8/1988 | Margolin | G02B 6/06 250/227.2 |
| 4,849,626 A | | 7/1989 | Franklin, Jr. | |
| 5,327,514 A | * | 7/1994 | Dujon | G02B 6/06 348/E5.028 |
| 5,515,470 A | * | 5/1996 | Eikelmann | G02B 6/04 250/227.2 |
| 5,930,433 A | * | 7/1999 | Williamson | G02B 6/06 356/444 |
| 6,587,189 B1 | | 7/2003 | Roberts et al. | |
| 6,743,337 B1 | * | 6/2004 | Ischdonat | D21G 9/0009 162/198 |
| 6,791,072 B1 | | 9/2004 | Prabhu | |
| 6,849,843 B2 | | 2/2005 | Ansorge et al. | |

(Continued)

FOREIGN PATENT DOCUMENTS

AT   408 385 B    11/2001
WO   00/66998 A2  11/2000

*Primary Examiner* — Rodney Fuller
(74) *Attorney, Agent, or Firm* — Seed IP Law Group LLP

(57) ABSTRACT

A bore imaging system comprises a photo detector having a readout set of pixels, and a bore surface imaging arrangement that transmits image light from the bore surface to the photo detector. The bore surface imaging arrangement comprises an image geometry transforming fiber bundle comprising a plurality of optical fibers having input ends that are arranged in a first shape to receive light that arises from an image zone and passes through a lens arrangement, and output ends that are arranged in a second shape to transmit the image light to the readout set of pixels, wherein the outputs ends or the readout set of pixels are configured such that at least 25% of the readout set of pixels receive the transmitted image light. High image data rates and good image resolution may thereby be provided in a borescope without using custom photo detectors.

22 Claims, 5 Drawing Sheets

(56) References Cited

U.S. PATENT DOCUMENTS

| | | | |
|---|---|---|---|
| 7,636,204 B1 | 12/2009 | Bourget | |
| 7,786,421 B2 | 8/2010 | Nikzad et al. | |
| 8,334,971 B2 | 12/2012 | Keller et al. | |
| 8,372,726 B2 | 2/2013 | de Graff et al. | |
| 8,570,505 B2 | 10/2013 | Baleine et al. | |
| 8,742,325 B1* | 6/2014 | Droz | G01J 1/0448 250/239 |
| 9,654,741 B2* | 5/2017 | Baleine | H04N 7/183 |
| 2002/0076178 A1* | 6/2002 | Klocek | A61B 5/015 385/106 |
| 2004/0247268 A1* | 12/2004 | Ishihara | A61B 5/0062 385/117 |
| 2004/0249247 A1* | 12/2004 | Iddan | A61B 1/0005 600/170 |
| 2005/0109918 A1* | 5/2005 | Nikzad | H01L 27/14683 250/208.1 |
| 2006/0274171 A1* | 12/2006 | Wang | G06K 7/14 348/294 |
| 2010/0264502 A1 | 10/2010 | Christophersen et al. | |
| 2012/0261551 A1 | 10/2012 | Rogers | |
| 2013/0112881 A1 | 5/2013 | Rudolf | |
| 2014/0276111 A1* | 9/2014 | Gal | A61B 1/00167 600/478 |
| 2016/0309065 A1* | 10/2016 | Karafin | G02B 6/32 |
| 2017/0097306 A1* | 4/2017 | Ullrich | G01N 21/954 |

\* cited by examiner

BORE IMAGING SYSTEM

BACKGROUND

Technical Field

The present application relates generally to bore inspection systems and more particularly to bore imaging systems.

Description of the Related Art

Various bore imaging systems are known that use a bore surface imaging arrangement for imaging the interior of a bore, for example in a cylinder bore of an engine. Exemplary bore inspection systems are disclosed in U.S. Pat. No. 4,849,626 (the '626 patent); U.S. Pat. No. 7,636,204 (the 204 patent); U.S. Pat. No. 8,334,971 (the '971 patent); U.S. Pat. No. 8,570,505 (the '505 patent); and U.S. Patent Application No. 2013/0112881, each of which is hereby incorporated herein by reference in its entirety. Such bore imaging systems may be configured to provide a 360-degree view (also referred to as a panoramic view and/or image) of the interior of a bore in order to inspect for form errors or surface defects. Some such systems use high-resolution optics. In any case, such systems may use signal processing to map image pixel signals or detector element signals to coordinates within the interior of the bore. In some such systems, a panoramic image of an approximately annular portion of a bore may be projected onto a two-dimensional (2-D) rectangular imaging array in a circular pattern corresponding to the shape of the annular portion. The circular or annular image pixels may then span a relatively large set of pixels (e.g., most of the rectangular imaging array) while actually imaging onto only a relatively small proportion of that set of pixels (e.g., an annular image pattern within the rectangular imaging array). A typical imaging array must read out each pixel spanned by the circle or annulus, even though pixels inside or outside of the annular image pattern are not relevant to inspection of the bore. Continuously reading out irrelevant pixels takes time, which limits the speed with which such a bore imaging system may be used to inspect a bore. Some systems (e.g., as disclosed in the '626 patent) have used fiber optic imaging paths, and routed each fiber to a corresponding photo detector. However, configurations of such systems have also imposed speed limitations, as well as imaging limitations that have limited resolution and/or versatility with regard to the range of bore sizes that may be inspected using a given system.

A non-contact, high-speed, high-resolution, metrology grade bore imaging system which solves the problems outlined above would be desirable.

BRIEF SUMMARY

A bore imaging system is disclosed that comprises a photo detector comprising a readout set of pixels, and a bore surface imaging arrangement configured to transmit image light arising from an image zone on the bore surface to the photo detector, the image zone having a shape characterized by a relatively narrow image dimension along an axial direction of the bore and a relatively elongated image dimension along a direction transverse to the axial direction of the bore. The bore surface imaging arrangement comprises an image geometry transforming fiber bundle comprising a plurality of optical fibers having input ends and output ends, and a lens arrangement (which may comprise an aperture or apertures) located along an optical path between the fiber ends and the bore surface. The input ends are configured in an input shape that approximately maps to a shape of the image zone, including a relatively narrow input dimension along a first direction that maps to the axial direction and a relatively elongated input dimension along a second direction transverse to the first direction. The input ends are arranged to receive image light that arises from the image zone and passes through the lens arrangement. The output ends of the image geometry transforming fiber bundle are arranged in a conjugate plane of, or proximate to, the readout set of pixels to relay or transmit the image light to the readout set of pixels, wherein at least one of a) the outputs ends or b) the readout set of pixels are configured such that at least 25% of the readout set of pixels receive the transmitted image light. In various embodiments, such a system provides a high throughput rate for meaningful image data, and a metrology grade imaging configuration that is versatile with regard to measuring a range of bore sizes with high resolution. In various embodiments, these benefits may be achieved without using a custom photo detector configuration. In various embodiments, the relatively elongated image dimension may cover 360 degrees around the bore. In various embodiments, the features disclosed herein allow the image zone to be scanned axially along the bore at an unprecedented rate.

BRIEF DESCRIPTION OF THE SEVERAL VIEWS OF THE DRAWINGS

The foregoing aspects and many of the attendant advantages will become more readily appreciated as the same become better understood by reference to the following detailed description, when taken in conjunction with the accompanying drawings, wherein.

DETAILED DESCRIPTION

Figure 1:
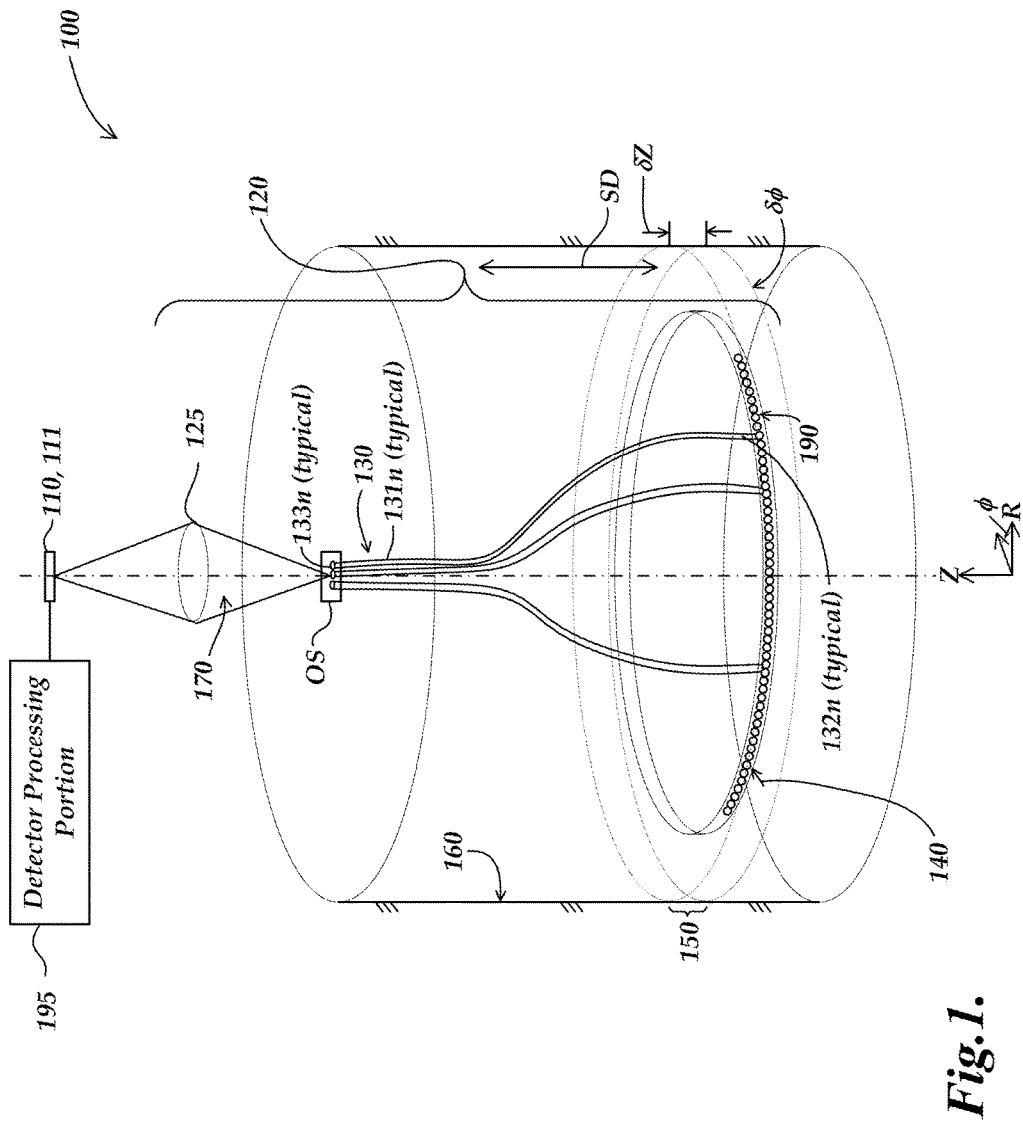
FIG. 1 is a schematic diagram of one embodiment of a bore imaging system according to principles disclosed herein.

FIG. 1 is a schematic diagram of one embodiment of bore imaging system 100 according to principles disclosed herein. The bore imaging system 100 comprises a photo detector 110, a bore surface imaging arrangement 120 and a detector processing portion 195. FIG. 1 is arranged according to cylindrical coordinates Z, R and φ, which are aligned with a cylindrical bore in this example. The photo detector 110 comprises a readout set of pixels 111, as described in greater detail below. The bore surface imaging arrangement 120 comprises an image geometry transforming fiber bundle 130 comprising a plurality of optical fibers 131 (e.g., 131n) having input ends 132 (e.g., 132n) and output ends 133 (e.g., 133n), and a lens arrangement 190 located along an optical path between the input ends 132n and a bore surface 160. In some embodiments, the geometry transforming fiber bundle 130 may comprise approximately 5,000 optical fibers 131. The embodiment of the bore surface imaging arrangement 120 shown in FIG. 1 also comprises an optional schematically illustrated relay lens configuration 125, which images the output ends 133 onto the readout set of pixels 111 along an output optical path. If desired, the relay lens configuration 125 may provide a desired magnification or demagnification, or variable magnification, in various embodiments. In some embodiments the relay lens configuration 125 may be omitted and the photo detector 110 may be located proximate to, or abutting, the output ends 133 such that the output optical path between the output ends 133 and the readout set of pixels 111 comprises no lenses.

In operation, the bore surface imaging arrangement 120 is configured to transmit image light 140 arising from an image zone 150 on the bore surface 160 to the photo detector 110, and in particular to the readout set of pixels 111. The image zone 150 has a shape characterized by a relatively narrow image dimension $\delta Z$ along an axial direction Z of the bore and a relatively elongated image dimension $\delta \varphi$ along a direction transverse to the axial direction Z of the bore. In the embodiment shown in FIG. 1, the image dimension $\delta \varphi$ spans the entire circumference of the bore surface 160. The input ends 132n are configured in an input shape that approximately maps to a shape of the image zone 150, including a relatively narrow input dimension along a first direction that maps to the axial direction Z and a relatively elongated input dimension along a second direction transverse to the first direction (i.e., that maps along the bore circumference direction of the image zone 150). In the illustrated example, the input shape is a cylinder or ring imaged by the lens arrangement 190. In the embodiment shown in FIG. 1, the first direction is approximately along the axial direction Z and the second direction is approximately along the direction corresponding to the $\varphi$ coordinate axis. The input ends 132n are arranged to receive image light 140 that arises from the image zone 150 and passes through the lens arrangement 190. The output ends 133n are arranged to transmit the image light 170 to the readout set of pixels 111 along an output optical path, e.g., using either the relay lens configuration 125 or a proximate detector, as outlined above. In various embodiments, in order to provide high image data throughput, at least one of a) the outputs ends 133n or b) the readout set of pixels 111 is configured such that at least 25% of the readout set of pixels receive the transmitted image light 170. In some embodiments, the readout set of pixels 111 is configured such that at least 50% of the readout set of pixels 111 receive the transmitted image light 170. In some embodiments, the readout set of pixels 111 is configured such that at least 75% of the readout set of pixels receive the transmitted image light 170.

It should be appreciated that the readout set of pixels 111 may be a subset of a total number of pixels of an imaging array of the photo detector 110. For example, some commercially available photo detector arrays may be controlled or configured to readout a selected or addressable subset of pixels that is less than all the pixels of the array. One such device is the Kodak KAI-0340 image sensor operating in a high frame rate partial scan mode of operation, available from Truesense Imaging, Inc., Rochester, N.Y., and others. A readout of a subset of pixels may be done in a shorter time interval than it takes to readout the entire array. In some embodiments, the readout set of pixels 111 may be less than half of the pixels of an imaging array. In some embodiments, the readout set of pixels 111 may be less than 25% of the pixels of an imaging array. In some embodiments, the readout set of pixels 111 may be less than 10% of the pixels of an imaging array. In some devices, the selected or addressable subset is desirably a block of contiguous pixels (e.g., due to device operating constraints or to provide the shortest readout time for a particular number of pixels.) In such a case, it may be optimal for the output ends 133 to be arranged in an output shape OS that approximately conforms to the shape of the readout subset of pixels, or that is otherwise selected to image the output ends 133 onto a desirable proportion of the readout set of pixels, in order to use readout time efficiently for meaningful image data according to principles disclosed herein.

An input end of a typical optical fiber typically has a high numerical aperture. For example, glass fibers may have a numerical aperture between 0.11 and 0.65. Therefore, if input ends of a fiber based imaging system are not in contact or very near contact with a bore surface, there may be "cross talk" between adjacent fibers, and poor imaging resolution. The lens arrangement 190 allows the bore imaging system 100 to image the bore surface 160 without requiring contact with the bore surface 160. In particular, the input ends need not be proximate to the bore surface, for example as taught in U.S. Pat. No. 4,849,626, which utilizes optical fibers carried on a mandrel which is in contact or very near contact with a bore surface, in order to provide an image. Such a bore imaging system must locate fiber ends close to the bore surface, e.g., 20-50 µm, which may be highly difficult to accurately align. Even so, the surface may be imaged with relatively poor lateral resolution. The lens arrangement 190 allows for a higher standoff from the bore surface 160, a greater depth of field, more forgiving alignment, and the ability to image a range of bore sizes.

It should be appreciated that for simplicity, illumination components are not shown in FIG. 1. Known illumination systems such as LED rings may be suitable for the bore imaging system 100. Exemplary LED rings are available from Schott Moritex of San Jose, Calif.

In the embodiment shown in FIG. 1, the input ends 132 are arranged to receive the image light 140 along a direction transverse to the axial direction Z, more specifically along an inward radial direction which may be along the direction R approximately normal to the bore surface 160. During operation, the input ends 132 and their associated optical components in the lens arrangement 190, discussed further below, are located at an operable imaging distance or focal length from the bore surface 160 as the bore surface imaging arrangement 120 moves along a scanning direction SD.

In some embodiments, the relay lens configuration 125 may have a magnification of −0.25.

In some embodiments, the input dimension $\delta Z$ of the shape of the image zone 150 provided by the lens arrangement 190 may be approximately 40 µm. The image zone 150 may span the entire circumference of a bore such that for a bore with a diameter of 80 mm, the input dimension $\delta \varphi$ is approximately 250 mm. In some embodiments, the image zone 150 may not span the entire circumference of a bore.

It should be appreciated that smaller fibers may be used to provide a higher resolution of imaging. In some embodiments, the optical fibers 131n may be less than 40 µm in diameter.

In the embodiment shown in FIG. 1, the lens arrangement 190 may comprise a microlens array. In alternative embodiments, the lens arrangement 190 may comprise an annular lens of constant cross section configured to focus rays within the R-Z plane.

Figure 5A:
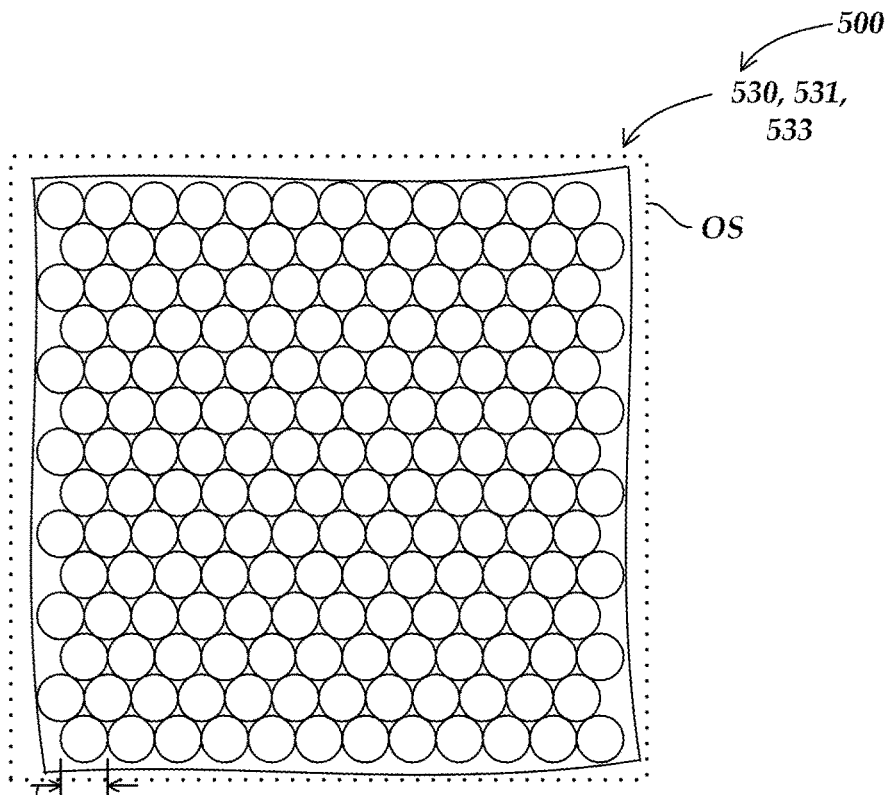
FIG. 5A is a schematic diagram of a first embodiment of the output ends of an image geometry transforming fiber bundle for a bore imaging system according to principles disclosed herein.

In the embodiment shown in FIG. 1, the input ends 132 are arranged in a circular shape. In some embodiments, the output ends 133n may be arranged in an output shape OS which is approximately rectangular (e.g., as shown in FIG. 5A), for reasons outlined above.

In some embodiments, the detector processing portion 195 may map pixels of the readout set of pixels 111 to respective locations in an unscrambled image of the image zone 150. A mapping relationship between the input end location and/or an image portion location of a conjugate plane corresponding to the image zone 150, and the output ends 133 and/or the pixels of the readout set of pixels 111, may be determined by known "calibration", correspondence, or mapping processes, for example as disclosed in U.S. Pat. No. 6,587,189 which is hereby incorporated herein by reference in its entirety. Such mapping may be performed at the time of fabrication of the system, or at another convenient time and place, and the resulting relationships stored in the system and used for real-time correspondence during use. The calibration need not be performed in the field by a user. In some embodiments, the detector processing portion 195 may be configured to reconstruct and display an image or image data corresponding to the image zone 150.

Figure 2A:
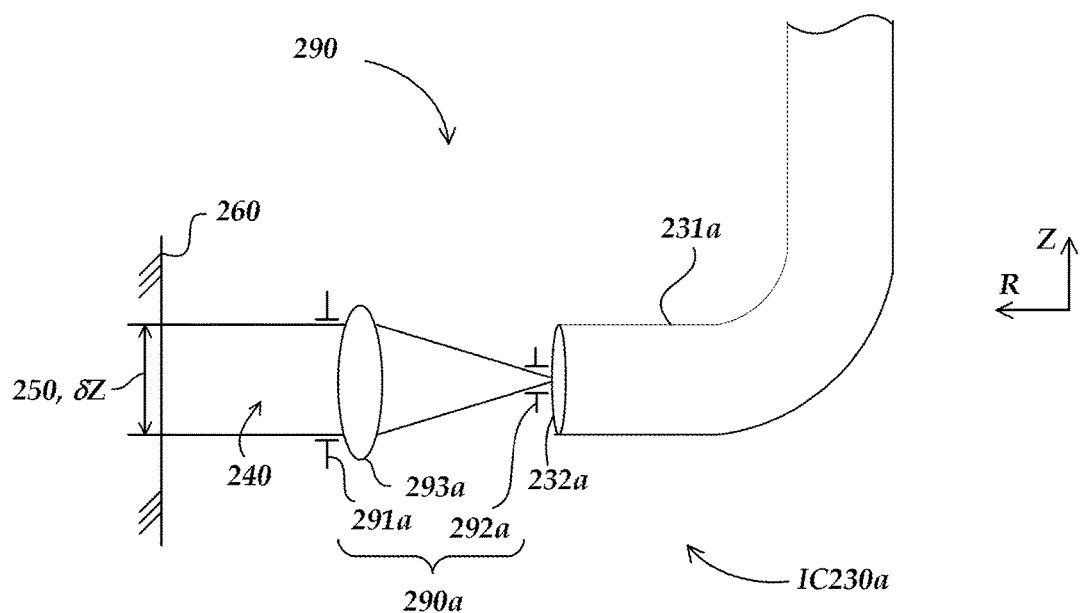
FIGS. 2A and 2B are schematic diagrams of a first embodiment of a lens arrangement usable in a bore imaging system according to principles disclosed herein.
Figure 2B:
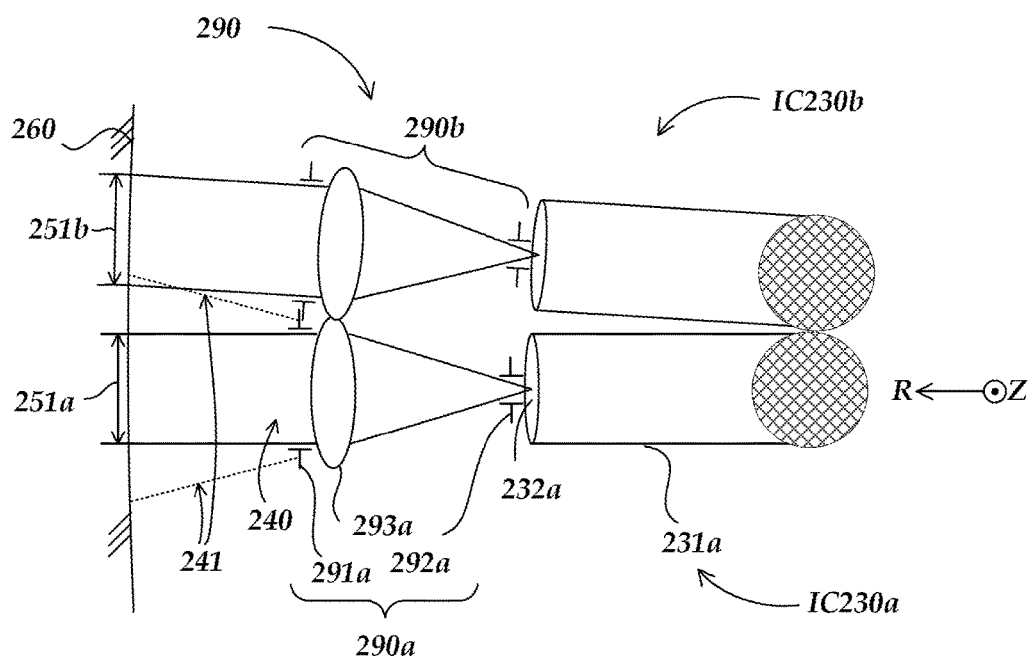

FIGS. 2A and 2B are schematic diagrams of a first embodiment of lens arrangement 290 usable as the lens arrangement 190 of the bore imaging system shown in FIG. 1. FIG. 2A shows components of one typical image channel IC230a associated with the optical fiber 231a included in a geometry transforming fiber bundle (e.g., similar to the geometry transforming fiber bundle 130 shown in FIG. 1). The geometry transforming fiber bundle and the associated lens arrangement 290 comprise a plurality of similar image channels. FIG. 2A shows a view along a direction normal to the R-Z plane of an image channel IC230a, and FIG. 2B shows a top view of two adjacent image channels IC230a and IC230b along a direction parallel to the axial direction Z. The portion of lens arrangement 290 associated with the image channel IC230a is designated 290a and comprises a limiting aperture 291a located in front of a microlens 293a and a limiting aperture 292a located at a back focal plane of the microlens 293a. The portion of lens arrangement 290 associated with the image channel IC230b is designated 290b. The image channel IC230a further comprises an input end 232a of a single fiber 231a located proximate to the limiting aperture 292a. The microlens 293a and the apertures 291a and 292a are configured to focus nominally collimated light 240 from an imaging zone 250 of a bore surface 260 into the input end 232a. In some embodiments, the microlens 293a may have a magnification of −1. Conversely, as shown in FIG. 2B, the limiting apertures 291a and 292a are configured to block non-collimated light such as the light rays 241 originating outside a field of view 251a from entering the image channel IC230a. This prevents light from a region which should nominally be imaged by an adjacent fiber (e.g., from a region in the field of view 251b of the image channel IC230b) from entering the input end 232a of the fiber 231a and therefore suppresses "image cross talk" between adjacent fibers. This may be understood to improve the lateral image resolution of the system. It will also be appreciated that such a lens arrangement also enhances the depth of field, allowing metrology grade imaging of a range of bore sizes.

Figure 3:
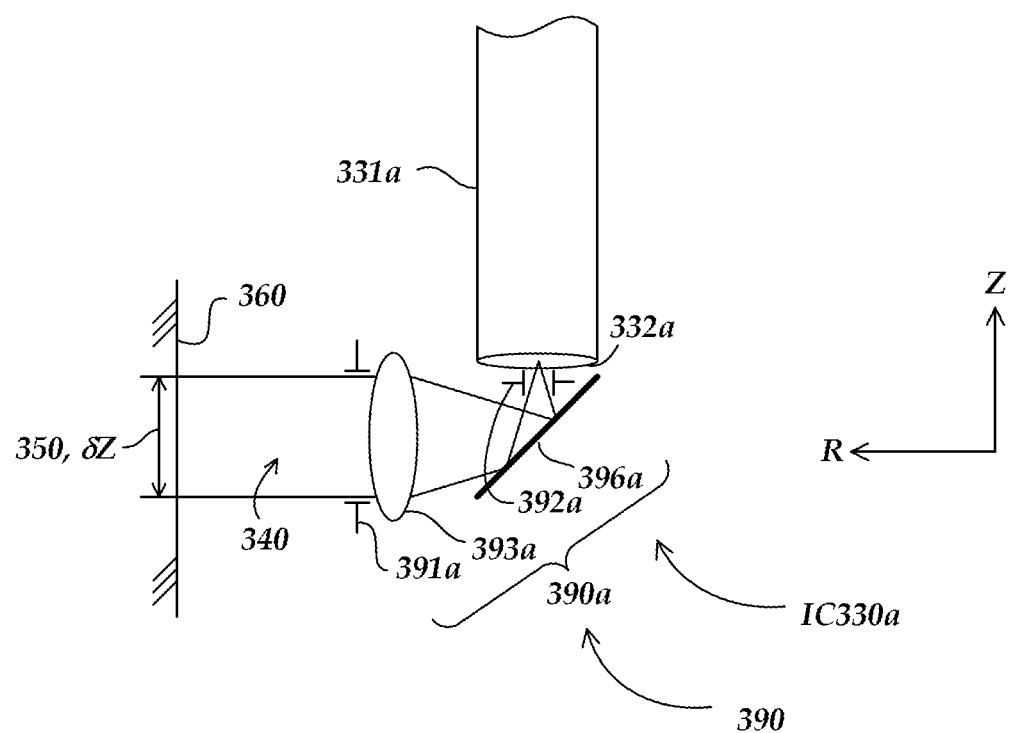
FIG. 3 is a schematic diagram of a second embodiment of a lens arrangement usable in a bore imaging system according to principles disclosed herein.

FIG. 3 is a schematic diagram of a second embodiment of a lens arrangement 390 usable as the lens arrangement 190 of the bore imaging system shown in FIG. 1. FIG. 3 shows components of one typical image channel IC330a associated with the optical fiber 331a included in a geometry transforming fiber bundle (e.g., similar to the geometry transforming fiber bundle 130 shown in FIG. 1). The geometry transforming fiber bundle and the associated lens arrangement 390 comprise a plurality of similar image channels. FIG. 3 shows a view along a direction normal to the R-Z plane, of an image channel IC330a. The lens arrangement 390 is similar to the lens arrangement 290 except for bend in the optical path provided by the reflector 396a, and operation of elements numbered 3XX may be understood by analogy to the description of the similarly numbered elements 2XX in FIGS. 2A and 2B. In the embodiment shown in FIG. 3, the input end of the single fiber 331a is not oriented normal to the bore surface 360. Rather, the reflector 396a is configured to reflect light from the microlens 393a into the input end 332a. In some embodiments, the microlens 393a may have a magnification of −1. In some embodiments, the reflector 396a may comprise an individual reflector. In other embodiments, the reflector 369a may comprise a portion of an annular reflector that provides similar portions for other imaging channels. In various embodiments, an assembly scaffolding for assembling and/or holding various components shown in FIGS. 1-3 in the proper relationship may be fabricated by 3-D printing or the like.

In the embodiment shown in FIG. 2A, individual fibers (e.g., the single fiber 231a) may be bent such that their respective input ends (e.g., the input end 232a) face outward in the R direction. However, individual fibers may have a minimum allowable bend radius, and size constraints within some bore imaging systems may prevent the individual fibers from bending to face outward in the R direction since it would require a small bend radius. A typical minimum bend radius of plastic optical fibers may be 0.4 mm, which may be suitable for the embodiment shown in FIG. 2A. A typical minimum bend radius of glass optical fibers may be 30 mm. Therefore, in some embodiments which may utilize glass fibers the embodiment shown in FIG. 3 may be advantageous for avoiding this design constraint and providing systems that may be adapted to inspect smaller bores.

Figure 4:
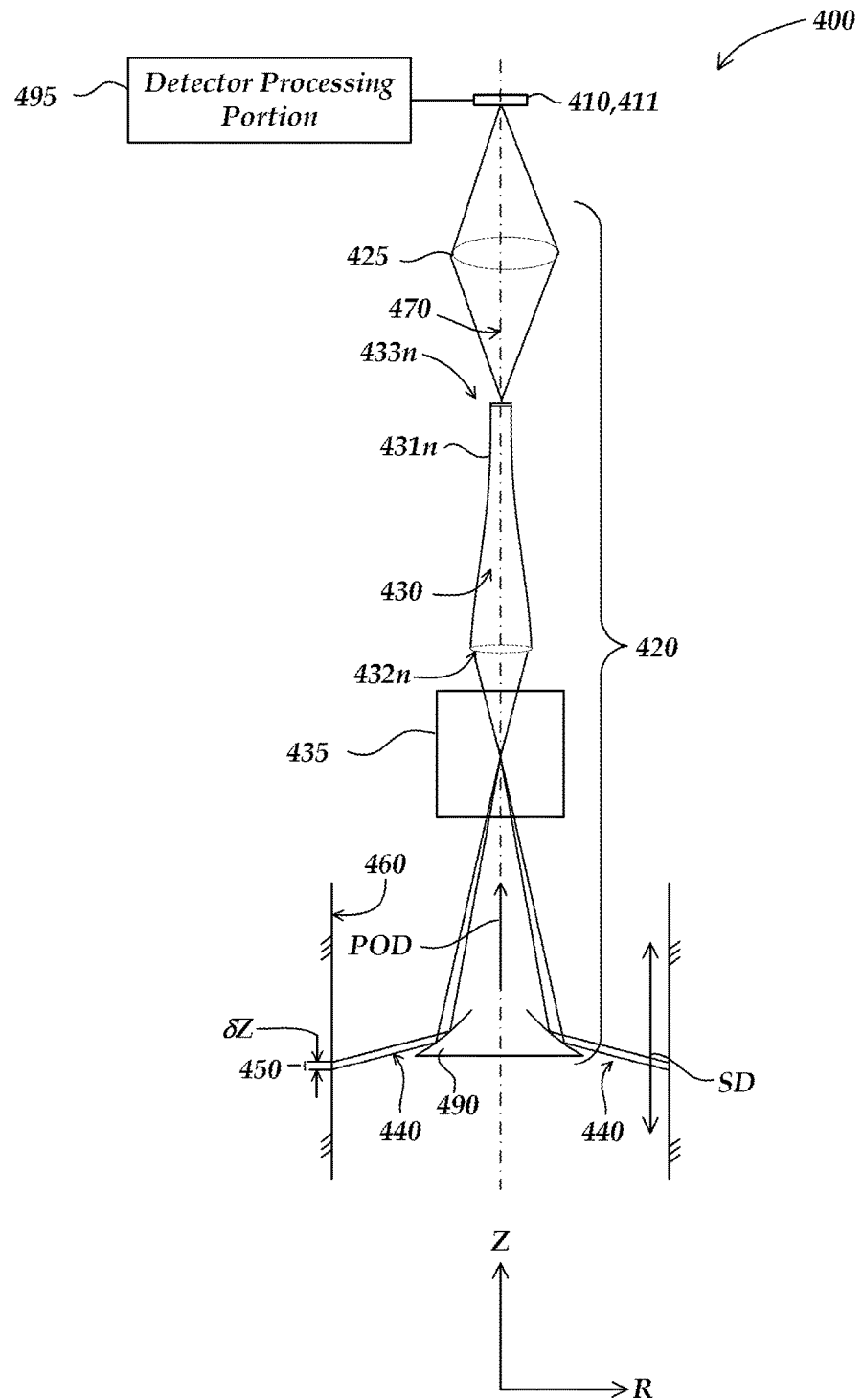
FIG. 4 is a schematic diagram of another embodiment of a bore imaging system according to principles disclosed herein.

FIG. 4 is a schematic diagram of a further embodiment of a bore imaging system 400. The bore imaging system 400 comprises a photo detector 410, a bore surface imaging arrangement 420 and a detector processing portion 495. FIG. 4 is arranged according to cylindrical coordinates Z, R and φ which are aligned with an axis of a bore. The photo detector 410 comprises a readout set of pixels 411. The bore surface imaging arrangement 420 comprises an image geometry transforming fiber bundle 430 comprising a plurality of optical fibers 431 (e.g., 431n) having input ends 432 (e.g., 432n) and output ends 433 (e.g., 433n), and a lens arrangement 490 located along an optical path between the input ends 432 and a bore surface 460. The lens arrangement 490 comprises a panoramic lens. In some embodiments, the geometry transforming fiber bundle 430 may comprise approximately 6,000 optical fibers 431. The bore surface imaging arrangement 420 also comprises relay lens 425 and imaging optics 435.

In operation, the bore surface imaging arrangement 420 is configured to transmit image light 440 arising from an image zone 450 on the bore surface 460 to the photo detector 410, and in particular to the readout set of pixels 411. The input ends 432 are arranged to receive image light 440 that arises from the image zone 450 and passes through the lens arrangement 490. More specifically, the lens arrangement 490 is configured to input the image light 440 along a direction R transverse to the axial direction Z, deflect the image light 440, and output the image light 440 along a panoramic output direction POD to the relay optics 435. In the embodiment shown in FIG. 4, the panoramic output direction POD is approximately parallel to the axial direction Z. The relay optics 435 are configured to demagnify the image light 440 and transmit it to the input ends 432 of the optical fibers 431. The output ends 433 are arranged to transmit the image light 470 to the readout set of pixels 411 along an output optical path, e.g., using either the relay lens 425 or a proximate detector, as outlined previously. In various embodiments, in order to provide high image data throughput, at least one of a) the outputs ends 433 or b) the readout set of pixels 411 is configured such that at least 25% of the readout set of pixels receive the transmitted image light 470. The relay lens 425 is configured to input the image light 470 from the output ends 433 and output the image light 470 to the readout set of pixels 411.

In some embodiments, during operation, the bore imaging system 400 is moved along a scanning direction SD to provide images that cover the bore along the axial direction. In alternative embodiments, the bore surface imaging arrangement 420 may comprise image path adjustment elements comprising deformable and/or coordinated movable imaging elements that deflect the field of view and focus of the system axially along the bore without having to move the entire bore surface imaging arrangement 420 along the scanning direction SD to do so. Such a system may provide faster scanning speed or mechanical response time for relocating the image zone 450. Using modern optical design simulation software and/or ray tracing programs, various configurations for such a system may be realized by one of ordinary skill in the art of optical design.

The image zone 450 has a shape characterized by a relatively narrow image dimension $\delta Z$ along an axial direction Z of the bore and a relatively elongated image dimension $\delta \varphi$ along a direction transverse to the axial direction Z of the bore. In the embodiment shown in FIG. 4, the first direction is approximately along the axial direction Z and the second direction is approximately along the direction corresponding to the $\varphi$ coordinate axis. The input ends 432 are configured in an input shape that approximately maps to a shape of the image zone 450. The input shape is an annulus imaged by the lens arrangement 490 in the illustrated embodiment.

It should be understood that in FIG. 4 the lens arrangement 490 is reflective. Other types of panoramic lenses suitable for a bore imaging arrangement such as a refractive fisheye lens may be understood from U.S. Pat. No. 8,334,971, which is incorporated by reference in entirety.

In some embodiments, the lens arrangement 490 and imaging optics 435 may provide a magnification of −0.5. The relay lens 425 may have a magnification of −0.9. For bore inspection operations with a 40 µm sampling resolution in the image zone 450, the optical fibers 431 may have a core size of 20 µm. For inspection of a typical bore with a diameter of 80 mm, the image geometry transforming fiber bundle 430 may have a width of 40 mm proximate to the input ends 432. In the embodiment shown in FIG. 4, the input ends 432 are arranged in a circular shape facing the axial direction Z.

For a bore with a stroke value of 160 mm, an input dimension $\delta Z$ in the axial direction Z of 0.04 mm, and an imaging rate of 1,250 frames per second, the bore imaging system 400 may be capable of scanning the engine bore in 3.2 s.

FIG. 5A is a schematic diagram of a first embodiment of the output ends of an image geometry transforming fiber bundle for a bore imaging system 500 according to principles disclosed herein. FIG. 5A shows output ends 533 of optical fibers 431 of a geometry transforming fiber bundle 430 which may be similar to the geometry transforming fiber bundle 130 or the geometry transforming fiber bundle 430.

Figure 5B:
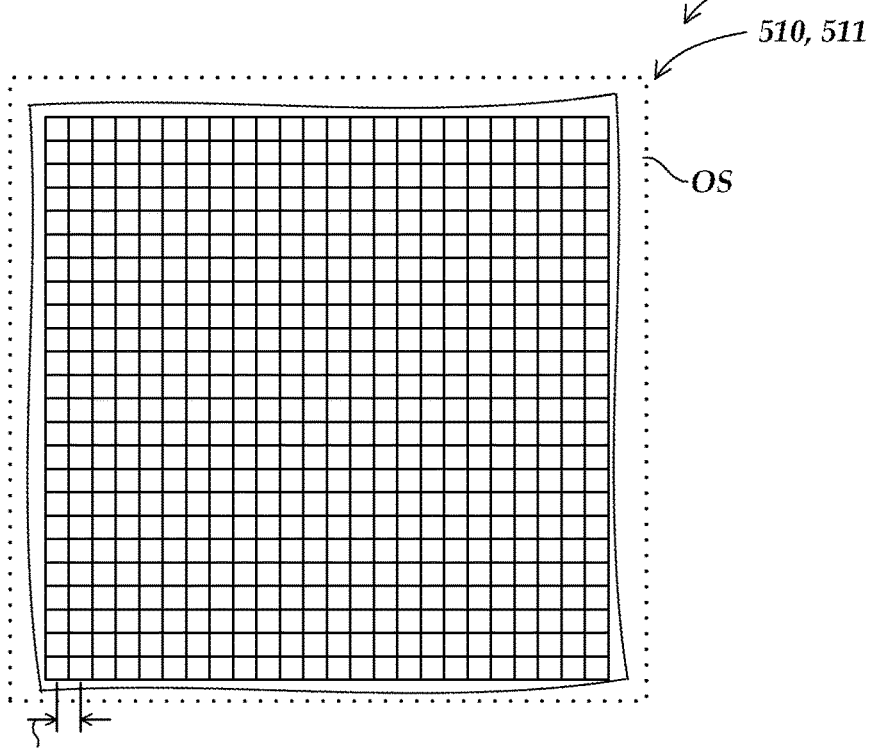
FIG. 5B is a schematic diagram of a first embodiment of readout set of pixels for a bore imaging system according to principles disclosed herein.

FIG. 5B is a schematic diagram of a first embodiment of readout set of pixels 511 for the bore imaging system 500 according to principles disclosed herein. FIG. 5B shows a portion of a photo detector 510, which may be similar to the photo detector 110 or the photo detector 410, comprising a readout set of pixels 511.

As shown in FIGS. 5A and 5B, the output ends 533 of the image geometry transforming fiber bundle 530 are arranged in an output shape OS that maps onto the readout set of pixels 511. The output ends 533 are conveniently arranged in a close packed arrangement of the individual fibers 531, although this arrangement is exemplary only, and not limiting. The output shape OS therefore comprises close packed fibers which are confined within a rectangular shape or outline. The readout set of pixels 511 also comprises a rectangular shape which matches the output shape OS.

It should be appreciated that the output ends 533 are shown in FIG. 5A as a small 12×14 group for simplicity. This small group may be understood to represent close packed bundle comprising a greater number of optical fibers arranged and confined corresponding to the shape of a readout set of pixels, according to the principles outlined above. Similarly, the readout set of pixels 511 is shown in FIG. 5B as a small 24×24 pixel group for simplicity. This small group may be understood to represent a greater number of pixels. A more typical array for a bore imaging system configured according to the principles described herein would be larger, to provide high-resolution metrology grade imaging, but fewer pixels than found in most non-custom photo detectors. For example, the readout set of pixels 511 may be a 224×160 pixel region of a larger pixel array, for example provided by a CCD such as a Kodak KAI-0340 image sensor operating in a high frame rate partial scan mode of operation to read out only the readout set of pixels.

However, this example is exemplary only and not limiting. In other embodiments, the readout set of pixels may comprise all the pixels of a suitable photo detector selected or designed to provide the desired resolution and readout rate.

In the embodiment shown in FIGS. 5A and 5B, each output end 533 has a minimum dimension $w_1$ which is at least 2 times a center-to-center distance $w_2$ of the pixels in the readout set of pixels 511. Thus, each fiber 531 corresponds to approximately four pixels. In some embodiments, a fiber may map to even more pixels. For example, in some embodiments a fiber may map to as many as six pixels. This may be advantageous in some embodiments as a simple means to insure that at least one pixel accurately samples the image intensity conveyed by a single fiber, without crosstalk from adjacent fibers.

While various embodiments have been illustrated and described, numerous variations in the illustrated and described arrangements of features and sequences of operations will be apparent to one skilled in the art based on this disclosure. Thus, it will be appreciated that various changes can be made therein without departing from the spirit and scope of the invention.

The invention claimed is:
1. A bore imaging system comprising:
a photo detector comprising a readout set of pixels, and
a bore surface imaging arrangement configured to transmit image light arising from an image zone on a bore surface to the photo detector, the image zone having a shape characterized by a relatively narrow image dimension along an axial direction of a bore and a relatively elongated image dimension along a direction transverse to the axial direction of the bore, wherein:

the bore surface imaging arrangement comprises:

an image geometry transforming fiber bundle comprising a plurality of optical fibers having input ends and output ends, wherein the input ends are configured in an input shape that approximately maps to a shape of the image zone, including a relatively narrow input dimension along a first direction that maps to the axial direction and a relatively elongated input dimension along a second direction transverse to the first direction, and a lens arrangement located along an optical path between the input ends and the bore surface and configured to reduce a numerical aperture of an input end of each of the optical fibers;

the input ends are arranged to receive the image light that arises from the image zone and passes through the lens arrangement; and the output ends are arranged to transmit the image light to the readout set of pixels along an output optical path, and at least one of a) the outputs ends or b) the readout set of pixels is configured such that at least 25% of the readout set of pixels receive the transmitted image light.

2. The bore imaging system of claim 1, wherein at least 50% of the readout set of pixels receive the transmitted image light.

3. The bore imaging system of claim 1, wherein at least 75% of the readout set of pixels receive the transmitted image light.

4. The bore imaging system of claim 1, wherein the output optical path comprises a relay lens arrangement that images the output ends onto the readout set of pixels.

5. The bore imaging system of claim 1, wherein the output ends are located proximate to or abutting the readout set of pixels and the output optical path comprises no lenses.

6. The bore imaging system of claim 5, wherein each output end has a minimum dimension which is at least 2 times a center-to-center distance of pixels in the readout set of pixels.

7. The bore imaging system of claim 1, further comprising a detector processing portion that maps pixels of the readout set of pixels to respective locations of their contribution to an unscrambled image of the image zone.

8. The bore imaging system of claim 1, wherein the readout set of pixels is a subset of a total number of pixels in the photo detector.

9. The bore imaging system of claim 1, wherein the readout set of pixels has a rectangular shape.

10. The bore imaging system of claim 1, wherein the output ends are arranged in a close packed arrangement.

11. The bore imaging system of claim 1, wherein the input ends are arranged to receive the image light along the direction transverse to the axial direction.

12. The bore imaging system of claim 1, wherein the input ends are arranged to receive the image light along a direction approximately normal to the bore surface.

13. The bore imaging system of claim 1, wherein the plurality of optical fibers are less than 40 µm in diameter.

14. The bore imaging system of claim 1, wherein the lens arrangement comprises one of a microlens array or an annular lens of constant cross section configured to focus within an axial plane.

15. The bore imaging system of claim 1, wherein the input ends are arranged in a circular shape.

16. The bore imaging system of claim 1, wherein the lens arrangement comprises a panoramic lens.

17. The bore imaging system of claim 16, wherein the lens arrangement inputs the image light along the direction transverse to the axial direction, deflects the image light, and outputs the image light along a panoramic output direction.

18. The bore imaging system of claim 16, wherein the input ends are arranged to receive the image light along the panoramic output direction.

19. The bore imaging system of claim 16, wherein the panoramic output direction is approximately parallel to the axial direction.

20. The bore imaging system of claim 1, wherein the lens arrangement comprises a microlens array including a plurality of microlenses, each microlens being configured and arranged to focus light from an adjacent region on the bore surface into an input end of a single optical fiber.

21. The bore imaging system of claim 20, wherein the microlens has a magnification of −1.

22. The bore imaging system of claim 20, wherein each microlens is associated with one or more apertures positioned relative to the microlens.

* * * * *